United States Patent [19]

Karaev et al.

[11] Patent Number: 5,705,687
[45] Date of Patent: Jan. 6, 1998

[54] NEUROTROPIC DRUG AND METHOD FOR PREPARATION OF SAME

[75] Inventors: Andrei Lvovich Karaev; Vladimir Mikhailovich Avakumov; Galina Sergeevna Kozlova; Olga Ivanovna Semina; Vladimir Ivanovich Gunar, all of Moskow, Russian Federation

[73] Assignee: Nauchno-Proizvodstvennoe Obiedinenie "Vitaminy", Russian Federation

[21] Appl. No.: 571,920

[22] PCT Filed: Jun. 28, 1994

[86] PCT No.: PCT/RU94/00139

§ 371 Date: Mar. 20, 1996

§ 102(e) Date: Mar. 20, 1996

[87] PCT Pub. No.: WO95/01169

PCT Pub. Date: Jan. 12, 1995

[30] Foreign Application Priority Data

Jun. 30, 1993 [RU] Russian Federation ............ 93033744

[51] Int. Cl.[6] ................................. C07C 229/00
[52] U.S. Cl. ............................................. 562/567
[58] Field of Search ................................. 562/567

[56] References Cited

FOREIGN PATENT DOCUMENTS

| | | |
|---|---|---|
| A20004649 | 10/1979 | European Pat. Off. . |
| 1170132 | 2/1967 | United Kingdom . |
| 1313821 | 4/1973 | United Kingdom . |
| 2135300 | 8/1984 | United Kingdom . |

*Primary Examiner*—Michael L. Shippen
*Attorney, Agent, or Firm*—Nixon & Vanderhye

[57] ABSTRACT

A new chemical compound, ketopantoyl aminobutyrate of formula I:

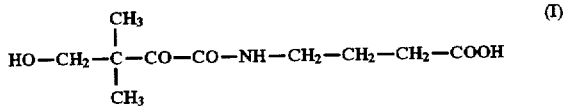

and its salts.

The compound is obtained by interaction of ketopantolactone and a salt of γ-aminobutyric acid.
It was shown that the new compound exhibits sedative, anti-amnesic and antihypoxic properties.

6 Claims, No Drawings

NEUROTROPIC DRUG AND METHOD FOR PREPARATION OF SAME

TECHNICAL FIELD

The invention relates to the field of medicine, more specifically to the pharmaceutical field, in particular, to a new neurotropic drug which affects the central nervous system and may be used in neurology, psychiatry, including in the treatment of Alzheimer' diseases

BACKGROUND

The invention concerns new derivatives of γ-aminobutyric acid. This acid, known as a preparation under the name of aminalon (gammalon), exhibits neurotropic activity and is used in the practice of medicine. However, it does have a number of disadvantages, such as a low activity level, side effects and a narrow spectrum of action which limits its applications.

Of the various derivatives of the γ-aminobutyric acid currently in use as neurotropic agents, calcium salt of the D-homopantothenic acid, known under the commercial name of "pantogam", is most closely related to the agents of the present invention. (M. D. Mashkovsky, Pharmaceutical Drugs, Moscow, Meditsina, 1986, vol. 1, page 624; Y. Nishizawa, Studies on homopantothenic acid, Medical Journal, Osaka, University, 1984, vol. 35, No. 1,2, pp. 41–50). Pantogam, when compared to aminalon, has superior properties due to better penetration of the hematoencephalitic barrier, which results in higher effectiveness and a wider range of action, at the same time exhibiting sedative and other neurotropic properties. (T. A. Voronina, T. L. Garibova, I. V. Khromova, U. M. Tilekeeva, Dissociation of Anti-amnesic and Antihypoxic Effects of Nootropic and Antihypoxic Drugs, Pharmacology and Toxicology, 1987, No. 3, pp. 21–24).

However, this drug also has several disadvantages. A therapeutic effect is achieved only by administration of a high dose of the drug, up to 3 grams a day. Consequently, it has a very low therapeutic index (3.3), and may sometimes have undesirable side effects, such as depression and myorelaxation.

Furthermore, one of the components of pantogam is the expensive D-pantolactone, which is derived by the separation of the synthetic DL-pantolactone into enantiomers. This multi-stage process involves difficult-to-obtain, toxic and flammable substances and solvents, and results in a considerable amount of waste.

DISCLOSURE OF THE INVENTION

To overcome the disadvantages of the known neurotropic agents, it is the object of this invention to create an effective drug suitable for a broad range of applications, characterized by a low level of toxicity and a high therapeutic index, effective in small doses and with no undesirable side effects.

Another object of this invention is to create the neurotropic agents having the above pharmacological advantages with a simple, safe and inexpensive technological process.

Both of the aforementioned objects are solved by the invention by creating new derivatives of the γ-aminobutyric acid: N-(4-hydroxy-3,3-dimethyl-2-oxo-1-butyryl)γ-aminobutyric acid (formula I), ketopatoyl aminobutyrate.

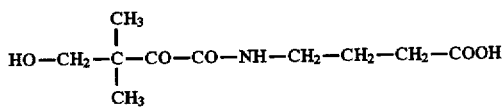

and its pharmaceutically acceptable salts.

The new compounds are characterized therein that they include among their constituents, the keto(oxo)pantoic and the γ-aminobutyric acids, which together form an amide bond.

Unexpectedly, the new compounds have demonstrated a therapeutic index two orders higher than that of their analogue, pantogam and the therapeutic index for the subject compounds is over 100. As well, the desired effect was achieved at dosages a whole order lower than those of pantogam. Furthermore, the synthesized compounds have exhibited a broad scope of activity in the central nervous system (sedative as well as anti-amnestic and antihypoxic effects were also observed).

The aforementioned properties are not only characteristic of the ketopantoyl aminobutyrate compound, but also its various salts, in particular, those of calcium and magnesium. Of all the salts derived, however, the best properties were demonstrated by the calcium salt of the synthesized acid.

The second object, that of improving the technological process for preparing the drug of the invention, was solved by substituting ketopantolactone for one of the components in the synthesis, the D-pantolactone, used for producing pantogam. The production of the latter excludes the separation of enantiomers, thereby improving the cost effectiveness of the entire product, rendering the technological process less harmful to the environment by decreasing the mount of waste, eliminating the need for great quantities of raw materials and solvents, and decreasing power requirements.

The new compound, ketopantoic aminobutyrate, is obtained by condensation of the ketopantolactone in a mixture of a salt of the γ-aminobutyric acid and alcohol, and by subsequently treating the resultant product with an organic or mineral acid or cation exchange resin hydrogen ion form.

The process, by which salts of ketopantoyl aminobutyrate are derived, excludes any treatment of the resultant product with either acid or sulfocationite.

The chemical structure of the ketopantoyl aminobutyrate and its salts have been verified through element analysis and IR-spectra. Ketopantoyl aminobutyrate is a colourless viscous liquid, readily soluble in water and alcohol, but not in acetone or chloroform.

The calcium and magnesium salts of ketopantoyl aminobutyrate are in the form of whim hygroscopic powders, readily soluble in water and alcohol, but not in acetone or chloroform.

PREFERRED EMBODIMENTS OF THE INVENTION

Hereinafter, abbreviations will be used for the following terms:
KPA Ketopantoyl aminobutyrate
KPA-Ca calcium salt of ketopantoyl aminobutyrate
KPA-Mg magnesium salt of ketopantoyl aminobutyrate.
Examples 1–4 shall illustrate the preparation of the compounds of the invention.

EXAMPLE 1

1.02 g (0.025 gram molecule) of metallic calcium is heated in 25 ml of methanol, for one hour, then 5.26 g (0.05 gram molecule) of γ-aminobutyric acid are added and the mixture is stirred for one hour at 65° C. 6.54g (0.05 gram molecule) of ketopantolactone are added and the mixture is stirred for 1.5 hours at 65° C. Methanol is then distilled to a syrup-like residue and 50 ml of acetone is stirred in at room temperature. The product is then filtered, washed, through with acetone, then dried. 10.71 g of KPA-Ca is obtained. The yield is 85.6%. The melting point is 208°–211° C. Found (in %): C 47.35; H 6.51; N 5.31: $C_{20}H_{32}O_{10}N_2Ca$. Calculated for (in %): C 48.00; H 6.44; N 5.59.

IR spectrum: 3400 cm$^{-1}$ (OH, NH); 1700 cm$^{-1}$ (v__C=O); 1660 cm$^{-1}$ (v__CO amide I); 1560 cm$^{-1}$ (v CN amide II).

EXAMPLE 2

1.43 g (0.025 gram molecule) of calcium oxide is added to 5.26 g (0.05 gram molecule) of γ-aminobutyric acid in 25 ml of methanol. This mixture is stirred for one hour at 65° C. 6.54 g (0.05 gram molecule) of ketopantolactone are added and stirred for one hour at 65° C. The methanol is then distilled off, the residue is dissolved in 40 ml of water and extracted with chloroform. The acqueous layer is filtered through activated charcoal, evaporated and dried. 10.48 g of KPA-Ca is obtained. The yield is 83.8%. The melting point is 207°–210° C. (with decomposition).

EXAMPLE 3

1.03 g (0.025 gram molecule) of magnesium oxide is added to 5.26 g (0.05 gram molecule) of γ-aminobutyric acid in 25 ml of absolute ethyl alcohol, and the mixture is stirred for 30 min. at 60° C. The reaction mixture is then filtered through a layer of activated charcoal. 6.54 g (0.05 gram molecule) of ketopantolactone are then added to the filtrate and stirred for one hour at 65° C. Next, the solution is evaporated and the residue dried in a vacuum. 11.56 g (93.5%) of KPA-Mg is obtained. The melting point is 195°–198° C. (with decomposition).

EXAMPLE 4

10 g (0.02 gram molecule) of KPA-Ca, prepared as in Example 1, are dissolved in 50 ml of distilled water and passed through sulfocationite, in the form of H+. The cation exchange resin hydrogen ion form is then rinsed with water until every trace of KPA has been eliminated from the eluate. The eluate is then concentrated, until it reaches a volume of 50 ml, after which it is extracted with chloroform. The solution of KPA is then evaporated, and the residue dried in a vacuum. 8.22 g (0.035 gram molecule) of KPA is obtained. The yield is 89%.

The central neurotropic activity of the new compounds was analyzed and tested by conventional methods, conducted in laboratory tests on white crossbred mice of both genders weighting 20±2 g. The spontaneous motor activity (SMA) was measured in a 60 min. interval, with the 40-channel automatic motor meter, according to the method described in the paper by J. Knoll, Motormeter, a new sensitive apparatus for the quantitative measurement of hypermotility caused by phychostimulant, Arch. Internat. Pharmacodyn. Therap., 1961, No. 130, No. 1, pp. 141–154, in the revision by K. S. Rayevsky and V. L. Timofeev, Multi-channel apparatus for registering moto-activity of small laboratory animals, Bulletin (News release) of experimental biology, 1965, N 6, pp. 114–116. The method is based on the principle of an electrical circuit, closed and opened by the animals moving from one metal plate onto another. This test is commonly used for testing sensitivity of the central nervous system (CNS) and the changes which occur under the influence of the substance being studied, resulting in either a depressing or stimulating activity.

In order to assess the ability of the new compounds to interfere with the orientation reflexes (OR) of the animals, the latter were subjected to the test of "ascent onto an inclined net" (Boissier J. R. Sination libre et psychotropes: Pharmacology of conditioning learning and retention, Proc. of 2nd International Pharmacological Meeting, London, N.Y., 1965, pp. 25–38). Suppressing of "exploratory" behaviour of animals is indicative of specific psychotropic properties of the substance, and, to a certain extent, characterizes its depressing effect.

The myorelaxing effect of the new compounds was tested by the method of the "rotating rod"(Dunham N. W., Miga T. S., A note on a simplex apparatus for detecting neurological deficit in rat and mice, J. Am. Pharm. Ass., 1957, vol. 46, No. 3, pp. 208–209), which allows one to record any abnormalities in coordination and balance, as well as ataxia. The mice in the laboratory tests were placed on a horizontal rod, 2 cm in diameter, rotating at a speed of 5 revolutions per minute. The object was to register the number of mice which were able to maintain equilibrium on the rod for two minutes. Any presence of a myorelaxing component was considered to be a side effect of the substance being studied.

Determining the degree, to which a substance affects the duration of soporific activity produced by various barbiturates, is a conventional method in experimental psychopharmacology, used for initial identification of not only narcotic and soporific properties, but also of neuroleptic, tranquilizing, stimulating and other types of psychopharmacological activity, with one central active component.

Duration of the soporific activity of barbiturates (hexobarbital 100 mg/kg, i.p.; barbital sodium 250 mg/kg, i.p.) was recorded from the moment the animals had lost the rotation reflex to the moment it was restored.

The chemical substance, in an acqueous solution, was injected intraperitoneally, 60 min. before the start of the experiment. An exception was made for tests involving barbiturates, in which case the synthesized compound was injected 30 min. before the start of the experiment. Its activity level was compared to that of pantogam, administered in "equi-molar" dosages. The acute toxicity was measured in mice, injected with the substance in the abdominal area. The average lethal dose ($LD_{50}$) was calculated in accordance with the Litchfield-Wilcockson method.

The statistical analysis of the results of the experiments was carded out on a computer using the "Turbo-dost5" and "Symphony-Probit" programs.

The acute toxicity analysis of KPA-Ca showed that the $LD_{10}$ of this compound used on mice, injected intraperitoneally, is equal to 2234.3±60.7 mg/kg. Experiments conducted earlier with pantogam, administered under identical conditions, indicated the $DL_{50}$ of pantogam to be 2250 mg/kg. Therefore, the toxicity of both substances, when administered only once, is almost identical. However, the maximum tolerance level of pantogam is 1000 mg/kg, while that of KPA-Ca is 1500 mg/kg.

When injected intravenously, the $DL_{50}$ of KPA-Ca is 1039.4±13.5 mg/kg, and that of pantogam is 1075 mg/kg.

The study of motor activity in the SMA test has shown that KPA-Ca decreases the motor activity in the test animals. The average number of runs decreased considerably after the drug was administered, and the greatest effect was observed with a dose of 150 mg/kg. Pantogam, when injected, also had a depressing effect on motor activity, however, this effect was evident only when much higher doses were administered. E.g., The number of runs in the motor meter decreased by 30% after 500 mg/kg of pantogam were injected. The same result was achieved by injecting only 10 mg/kg of KPA-Ca. That is 50 times less than the pantogam dose. A 70% decrease in motor activity was produced by injecting 1000 mg/kg of pantogam, the maximum tolerable dose. It took only 150 mg/kg (exactly 10 times less than the maximum tolerable dose) of KPA-Ca to produce the same effect. (Table 1)

TABLE 1

Effect of pantogam and KPA-Ca on spontaneous motor activity in mice.

| Drug<br>1 | Dose<br>(mg/kg)<br>2 | Average<br>SMA, M ± _m<br>3 | Relative change in<br>activity (%)<br>4 |
|---|---|---|---|
| Control group | — | 632.8 ± 35.2 | 100 |
| KPA-Ca | 10 | 482.8 ± 101.8 | 76.3 |
| | 25 | 369.1 ± 68.7** | 58.3 |
| | 50 | 338.9 ± 74.5** | 53.6 |
| | 100 | 270.4 ± 75.3** | 42.7 |
| | 150 | 190.6 ± 28.2*** | 30.1 |
| Control group | 0 | 524.0 ± 99.2 | 100 |
| Pantogam | 500 | 392.0 ± 307 | 74.8 |
| | 1000 | 176.0 ± 116* | 33.6 |

Note: Hereinafter, an asterix is used to indicate statistically verified results:
* - where $P < 0.05$;
** - where $P < 0.01$;
*** - where $P < 0.001$.

The study of the effect the drugs have on the orientation reflexes of the animals, conducted in accordance with the "test of ascent onto an inclined net", have shown that KPA-Ca, when administered in dosages between 0.1 and 150 mg/kg, does not disturb the "exploratory" behaviour of the animals. Pantogam, on the other hand, suppressed the orientation reflex in mice. The drug reaches its maximum strength 60 min. after it has been administered. The average effective dose ($DE_{50}$) giving the maximum strength for pantogam is 680 (565–816) mg/kg.

Testing the effect KPA-Ca has on muscular strength and movement coordination, according to the method of the "rotating rod", has shown that the injection of the new substance in the same dosage range, did not induce any ataxia, myorelaxation or loss of movement coordination in the test animals during the entire test period (3.5 hours). At the same time, administering pantogam in doses of 300 mg/kg and higher resulted in the loss of movement coordination, which was seen as a side effect of the drug. The maximum strength of the drug was demonstrated 30 min. after the pantogam was injected and movement coordination and muscle strength did not return until 1.5 hours after the start of the experiment.

The analysis of the effect KPA-Ca has on the duration of the soporific action of barbiturates revealed that the new compound considerably prolongs the duration of sleep induced by barbiturates. In the case of barbital sodium, the effect of administering KPA-Ca in doses of 25, 50 and 1130 mg/kg, surpassed the parameters taken from the control group by 126.5, 95 and 129.3%. It should be noted that, at the same time, KPA-Ca decreases the amount of time it takes the animals to assume a lateral position. Depending on the dose, the effect varies in the range from 30.4 to 38.6 % of the control level. (Table 2).

TABLE 2

Effect of KPA-Ca on the soporific action of barbital sodium.

| Drug | Dose<br>mg/kg | Lateral position<br>(min) | %<br>effect | Duration of sleep<br>(min) | % effect |
|---|---|---|---|---|---|
| Barbitol sodium | 250 | 38.1 ± 1.3 | 100 | 159.2 ± 11.2 | 100 |
| KPA-Ca | 1 | 26.5 ± 1.9*** | 69.6 | 159.1 ± 12.6 | 99.9 |
| | 10 | 23.4 ± 1.5*** | 61.4 | 195.4 ± 12.1 | 122.7 |
| Barbitol sodium | 250 | 31.8 ± 1.1 | 100 | 53.5 ± 5.5 | 100 |
| KPA-Ca | 25 | 21.4 ± 0.6*** | 67.3 | 121.2 ± 12*** | 226.5 |
| Barbitol sodium | 250 | 34.5 ± 1.4 | 100 | 79.3 ± 8.1 | 100 |
| KPA-Ca | 50 | 23.7 ± 1.9** | 68.7 | 154.7 ± 10.3*** | 195.1 |
| | 100 | 23.0 ± 0.8*** | 66.7 | 181.8 ± 5.4*** | 229.3 |

Similar results were obtained with the hexobarbital sleep mode. KPA-Ca, depending on the dosage administered, prolonged sleep duration in mice. The maximum effect was produced when injecting 100 mg/kg, at which time the control group parameters were exceeded by 102.4%. As in the test with barbital sodium, when the dose was increased to above 100 mg/kg, there was not noticeable change in the effect. In this model the KPA-Ca had no effect on the lateral position. This parameter fluctuated at ±4.2% from the control group level. (Table 3).

TABLE 3

Effect of KPA-Ca on soporific action of hexobarbital.

| Drug | Dose<br>mg/kg | Lateral<br>Position<br>(min) | % effect | Duration<br>of sleep<br>(min) | % effect |
|---|---|---|---|---|---|
| Hexobarbital | 100 | 2.4 ± 0.15 | 100 | 46.3 ± 2.3 | 100 |
| KPA-Ca | 1 | 2.5 ± 0.17 | 104.2 | 44.6 ± 5.2 | 96.3 |
| | 10 | 2.4 ± 0.16 | 100 | 67.2 ± 4.3** | 145.1 |
| | 25 | 2.5 ± 0.2 | 104.2 | 60.6 ± 1.9*** | 130.9 |
| | 50 | 2.3 ± 0.15 | 95.8 | 70.7 ± 3.1*** | 152.7 |
| | 100 | 2.4 ± 0.22 | 100 | 93.7 ± 4.3*** | 202.4 |
| | 150 | 2.5 ± 0.34 | 104.2 | 86.4 ± 4*** | 186.6 |

This test demonstrated that the new compounds are superior to pantogam. As indicated earlier, pantogam when administered in the therapeutic dose of 500 mg/kg increased by 20% the soporific effect of barbital sodium, and by 40% the effect of hexobarbital. The KPA-Ca, on the other hand, at a level 10 times lower (50 mg/kg), increased the duration of sleep by 95.1% and 52.7%, respectively.

The antihypoxic properties of the new compounds were tested in the models of hypoxic normobaric, hemic and histotoxic hypoxia. The hypoxic (hypercapnic) normobaric hypoxia was induced by placing the mice in hermetically sealed transparent boxes, subdivided into compartments, 80 cm³ each. The animals were observed until all respiratory movements ceased. The hemic hypoxia was induced by the intraperitoneal administration of sodium nitrite in a dose of 400 mg/kg. The hystotoxic hypoxia was induced by the intraperitoneal administration of sodium nitroprussiate, in a dose of a 20 mg/kg dosage.

The analysis of antihypoxic properties of KPA-Ca in the various experimental models of hypoxia, demonstrated that, under the conditions of normobaric hypoxia, the new compound, when administered in doses in the range of 10 to 100 mg/kg, successfully extended the lifespan of the test animals by 35.8–46% as compared to the control group.

When used in the model of histotoxic hypoxia, the KPA-Ca produced similiar results. However, any statistically significant increase in the lifespan of animals was registered at doses of 50 and 100 mg/kg Coy 21.6% and 38.4%, respectively). KPA-CA, under the conditions of the hemic hypoxia model, showed little activity. Only at 100 mg/kg, did its effect actually increase by 19.9% (Table 4). It should be noted, that this test has not shown any considerable advantages of KPA-Ca over pantogam, with the exception of the fact that KPA-Ca produced results at significantly lower doses. E.g. pantogam, under the conditions of hystotoxic hypoxia, when administered in the following doses: 250, 500 and 1000 mg/kg increased the lifespan of test animals by 57% and 85%, respectively.

TABLE 4

Effect of KPA-Ca on the lifespan of mice with induced hypoxia.

| Drug | Dose (mg/kg) | Average lifespan (sec) | % effect (M ± m) |
|---|---|---|---|
| Normobaric hypoxia | | | |
| Control group | 0 | 411 ± 11.9 | 100 |
| KPA-Ca | 10 | 558 ± 21.5*** | 135.8 |
| | 25 | 570 ± 17.3*** | 138.7 |
| | 50 | 588 ± 22.4*** | 143.1 |
| | 100 | 600 ± 30.7*** | 146 |
| Histotoxic hypoxia | | | |
| Na-nitro-prussiate | 20 | 765 ± 38 | 100 |
| KPA-Ca | 10 | 798 ± 38 | 104.3 |
| | 25 | 855 ± 43.2 | 111.8 |
| | 50 | 930 ± 55.1* | 121.6 |
| | 100 | 1059 ± 64** | 138.4 |
| Hemic hypoxia | | | |
| Na-nitrite | 400 | 790.5 ± 21.1 | 100 |
| KPA-Ca | 10 | 777 ± 30.1 | 98.3 |
| | 25 | 780 ± 30.3 | 98.7 |
| | 50 | 819 ± 41 | 103.6 |
| | 100 | 948 ± 40.3** | 119.9 |

The effect produced by the new substance on the processes of the central nervous system was examined on the model of one-time training of mice, of conditioned reaction of passive avoidance (CPRA), where the amnesic effect was produced by electric shock. During the tests, a two-section chamber was used to condition a certain reflex to the lit and darkened sections. First, for two minutes, the amount of time was registered, that a mouse spent in the lit section before entering the darkened section. Then, while in the darkened section, the animal would receive a single electric shock through the electrode floor (training). The training was immediately followed by an electric shock (50 Hz, 0.2 see). Memory was tested after 24 hours for 2 minutes. The substance was intraperitoneally administered 40 min. prior to the start of the training, the control group received a physiological solution. The amnesic effect of the electric shock was demonstrated insofar that, when the animal was tested 24 hours after developing CRPA, it showed no signs of fear of entering into the darkened "dangerous" section. The anti-amnesic properties of the new compound are represented by an increase in the latent period before and after the training. (Δt)

TABLE 5

The effect of KPA-Ca on the latent period of CRPA.

| | | Latent period (sec) | | |
|---|---|---|---|---|
| Drug | Dose mg/kg | before training | after training | t ± _m, sec | % effect |
| Control group + amnesia | 0 | 34.1 | 31.1 | −3 ± 6 | 91.2 |
| Control group w/o amnesia | 0 | 29.4 | 84.7 | 55.3 ± 9.6*** | 288.1 |
| KPA-Ca | 10 | 27.1 | 90.3 | 63.2 ± 12.6** | 334.4 |
| | 25 | 31.4 | 102.4 | 71 ± 9*** | 396.1 |
| | 50 | 30.6 | 77.8 | 47.2 ± 13.3** | 254.2 |
| | 100 | 31.8 | 82.8 | 51 ± 14.1** | 260.4 |

The study of the anti-amnesic properties of KPA-Ca in the CRPA model illustrated that, in the control group of animals, application of electric shock had eradicated the acquired "skill" (taught by the electric current passed through the electrode floor). The latent period of time spent in the lit section of the chamber after 24 hours was 91.2%. In the control group of animals, not exposed to the effect of the electric shock, the latent period after the training had noticeably increased, by 288.1%. The administration of KPA-Ca had counteracted the amnesic effect of the electric shock and preserved the acquired "skills". This demonstrated the anti-amnesic properties of the tested substance (Table 5). Earlier tests of pantogam demonstrated that this drug, introduced in doses ranging from 250 to 500 mg/kg, has moderate a anti-amnesic effect, quantitatively representing 60–75% of the "model" latent period in animals not exposed to the electric shock.

INDUSTRIAL APPLICATION

Thus, results of the study of the pharmacological properties of the new compounds, carried out in accordance with the methods of neuropharmacological screening, have shown that the new compounds have the following advantages, as compared with analogue substances:

1. sedative activity, as demonstrated in tests with barbiturates and SMA, is evident at doses lower by a whole point,
2. absence of the suppressant component in the sedative activity, as demonstrated in the study of the orientation reflexes in the test of the "ascent on an inclined net",
3. absence of side effects, such as the myorelaxing activity, in the effective dosage range,
4. higher effectiveness, in quantitative terms, as demonstrated in all the tests of neuropharmacological screening,
5. broader therapeutic application of the new compound.

The new compounds have demonstrated sedative properties, and the combination of their antihypoxic and anti-amnesic characteristics gives grounds for considering KPA, as well as its salts, to be a nootropic drug. KPA, at the same time, had no depressing effect on the animals, which leads us to believe that there are no side effects in the examined dosage range.

Results of the conducted study show the new compound to be a promising neurotropic drug.

We claim:
1. A compound of formula I:

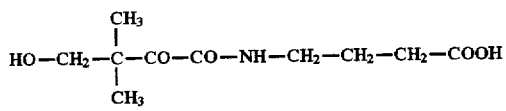

or a pharmaceutically acceptable salt thereof.

2. A compound according to claim 1, which is the calcium or magnesium salt of the compound of formula I.

3. A compound according to claim 2, which is the calcium salt of the compound of formula I.

4. Method for preparing a compound of formula I

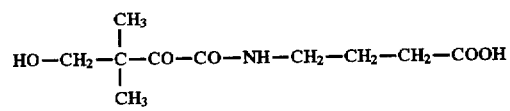

comprising condensing ketopantolactone with a salt of γ-aminobutyric acid, and thereafter treating the resultant salt product with an organic or mineral acid, or a cation exchange resin in hydrogen form.

5. Method for preparing a salt of the compound of formula I

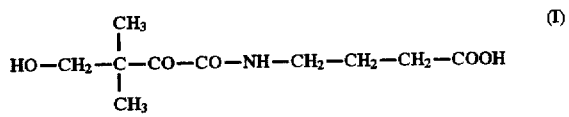

comprising condensing ketopantolactone with a salt of γ-aminobutyric acid.

6. A method according to claim 5, wherein the condensation is performed with a calcium salt of γ-aminobutyric acid in alcohol at a temperature of 60°–65° C.

* * * * *